(12) United States Patent
Lin et al.

(10) Patent No.: US 10,010,385 B2
(45) Date of Patent: Jul. 3, 2018

(54) DENTAL IMPLANT WITH CUSHION

(71) Applicant: JTI Biomed Corp., Tainan (TW)

(72) Inventors: Jiin-Huey Chern Lin, Winnetka, IL (US); Chien-Ping Ju, Kansas City, MO (US); Yen-Chun Chen, Kaohsiung (TW)

(73) Assignee: JTI BIOMED CORP., Tainan (TW)

( * ) Notice: Subject to any disclaimer, the term of this patent is extended or adjusted under 35 U.S.C. 154(b) by 318 days.

(21) Appl. No.: 14/398,490

(22) PCT Filed: May 3, 2013

(86) PCT No.: PCT/US2013/039366
§ 371 (c)(1),
(2) Date: Nov. 3, 2014

(87) PCT Pub. No.: WO2013/169569
PCT Pub. Date: Nov. 14, 2013

(65) Prior Publication Data
US 2015/0111178 A1    Apr. 23, 2015

Related U.S. Application Data

(60) Provisional application No. 61/643,511, filed on May 7, 2012.

(51) Int. Cl.
*A61C 8/00*    (2006.01)

(52) U.S. Cl.
CPC .......... *A61C 8/0066* (2013.01); *A61C 8/0018* (2013.01); *A61C 8/0039* (2013.01); *A61C 8/0078* (2013.01); *A61C 8/0086* (2013.01)

(58) Field of Classification Search
CPC ... A61C 8/0016; A61C 8/0057; A61C 8/0065; A61C 8/0086; A61C 8/066; A61C 8/0018; A61C 8/0039; A61C 8/0078
USPC ......................................... 433/173, 174, 177
See application file for complete search history.

(56) References Cited

U.S. PATENT DOCUMENTS

| | | | |
|---|---|---|---|
| 5,049,072 A * | 9/1991 | Lueschen | A61C 13/2656 433/173 |
| 5,282,746 A * | 2/1994 | Sellers | A61C 8/005 433/172 |
| 5,368,483 A | 11/1994 | Sutter et al. | |
| 5,527,182 A | 6/1996 | Willoughby | |
| 5,695,335 A * | 12/1997 | Haas | A61C 8/0086 433/169 |
| 6,283,754 B1 | 9/2001 | Wohrle | |
| 2006/0014120 A1* | 1/2006 | Sapian | A61C 8/0057 433/173 |
| 2008/0241790 A1* | 10/2008 | Gittleman | A61C 8/0053 433/174 |

(Continued)

*Primary Examiner* — Nicholas Lucchesi
(74) *Attorney, Agent, or Firm* — Bacon & Thomas, PLLC

(57) ABSTRACT

An dental implant has a substantially cylindrical hollow base member; an abutment; an implant-abutment junction (IAJ) portion at one end of the base member to retain the abutment to the base member, so that the abutment is able to move within a predetermined distance alone an axial direction of the base member, and a first cushion adapted to be mounted between the abutment and the base member for providing a resistance force when the abutment is pressed to move relatively toward the base member and providing a bouncing back force when the abutment is released from the pressing.

4 Claims, 15 Drawing Sheets

(56) References Cited

U.S. PATENT DOCUMENTS

2008/0261174 A1* 10/2008 Gittleman ............ A61C 8/0048
                                                    433/172
2009/0317769 A1    12/2009  Urdaneta
2010/0304334 A1    12/2010  Layton

* cited by examiner

US 10,010,385 B2

DENTAL IMPLANT WITH CUSHION

CROSS REFERENCE TO RELATED APPLICATIONS

This patent application claims the priority benefit of prior U.S. Provisional Patent Application Ser. No. 61/643,511 filed May 7, 2012.

FIELD OF THE INVENTION

The present invention is related to a dental implant, and in particular related to a dental implant with a cushion for absorbing impact force generated during chewing or biting.

BACKGROUND

In natural teeth the periodontal ligament functions as a cushion between tooth and jawbone, absorbing impact force and uniformly transferring occlusal forces to surrounding bone. The distribution of the force depends on micro movement induced by the periodontal ligament. Due to lack of periodontal ligament, dental implant has to directly bond to bone, causing non-uniform stress distribution in bone which might lead to implant failure (Quirynen 1992). Because of the lack of micro movement of implants, most of the force distribution is concentrated at the crest of the ridge. Vertical forces at the bone interface are concentrated at the crestal regions, and lateral forces increase the magnitude of the crestal force distribution.

The most common failure mode of dental implant is loosening of implant induced by the atrophy of surrounding jawbone, which is generally caused by improper stress distribution on cervical bone under occlusion or mastication loading. As mentioned earlier, overloading and stress shielding have often been cited as the primary biomechanical factors leading to marginal bone loss around implants (Cehreli and Akca). Whether the bone loss after implantation is due to overloading or stress shielding still needs to be clarified. No matter which effect (overstressing or stress shielding) dominates the long-term performance of dental implant, it seems logical that excessive stress concentrations (possibly resulting from non-axial overloading) plays a critical role in early-stage marginal bone loss process.

Overloading has been identified as a primary factor behind dental implant failure. The peak bone stresses normally appear in the marginal bone. The anchorage strength is maximized if the implant is given a design that minimizes the peak bone stress caused by a standardized load. The design of the implant-abutment interface has a profound effect upon the stress state in the marginal bone when this reaches the level of this interface.

SUMMARY OF THE INVENTION

The present invention provides an improved dental implant comprising:
a substantially cylindrical hollow base member comprising a wall defining a space in said substantially cylindrical hollow base member, and a plurality of through-thickness holes communicating said space with an outer surface of said wall;
an abutment;
an implant-abutment junction (IAJ) portion at one end of said base member to retain said abutment to said base member, so that said abutment is able to move within a predetermined distance alone an axial direction of said base member; and
a first cushion adapted to be mounted between said abutment and said base member for providing a resistance force when said abutment is pressed to move relatively toward said base member and providing a bouncing back force when said abutment is released from said pressing.

Preferably, wherein said abutment comprises a receiving part for receiving a dental prosthesis and a connecting part, wherein said IAJ portion has an axial hole and said connecting part of said abutment has a cylindrical rod portion having a diameter corresponding said axial hole and an enlarged end extending from said cylindrical rod portion, wherein said cylindrical rod portion is slidably received in said axial hole of said IAJ portion with said enlarged end protruding from one end of said axial hole and another end of said cylindrical rod portion protruding from the other end of said axial hole, wherein said IAJ portion is a separate part and threadedly connected to said one end of said base member, preventing said abutment from escaping said IAJ portion, and said first cushion is an elastomer and is sandwiched between said enlarged end of said connecting part of said abutment and said based member.

Preferably, said abutment comprises a receiving part for receiving a dental prosthesis and a connecting part having a cylindrical rod portion and an enlarged threaded end extending from said cylindrical rod portion, wherein said IAJ portion has an axial hole having a threaded inner wall portion corresponding to said an enlarged threaded end near an entrance of said axial hole and a smooth inner wall portion following the threaded inner wall portion having a diameter corresponding to that of said enlarged threaded end, wherein said enlarged threaded end is threaded through the threaded inner wall portion and into the smooth inner wall portion of said axial hole, and said first cushion is an elastomer and is sandwiched between said enlarged threaded end of said connecting part of said abutment and said based member.

Preferably, the dental implant of the present invention further comprises a C-shaped buckle, wherein said abutment comprises a receiving part for receiving a dental prosthesis and a connecting part having a cylindrical rod portion and an enlarged end extending from said cylindrical rod portion, wherein said C-shaped buckle is mounted on the cylindrical rod portion and between the enlarged end and the receiving part of said abutment, wherein said IAJ portion has an axial hole having an enlarged inner wall portion corresponding to said C-shaped buckle near an entrance of said axial hole and a smooth inner wall portion following the enlarged inner wall portion having a diameter corresponding to that of said enlarged end, wherein said C-shaped buckle is elastically clamped by the enlarged inner wall portion of said axial hole of said IAJ portion, and said first cushion is an elastomer and is sandwiched between said enlarged end of said connecting part of said abutment and said based member.

Preferably, the dental implant of the present invention further comprises an O-shaped buckle, wherein said abutment comprises a receiving part for receiving a dental prosthesis and a connecting part having a cylindrical rod portion, wherein said IAJ portion has an axial hole having an enlarged inner wall portion near an entrance of said axial hole and a smooth inner wall portion following the enlarged inner wall portion having a diameter corresponding to that of said cylindrical rod portion, wherein said O-shaped buckle has an inner diameter slightly smaller than that of the cylindrical rod portion and an outer diameter slightly smaller than that of the enlarged inner wall portion of said axial hole, and said cylindrical rod portion of said connecting part of said abutment is forced to insert into said O-shaped buckle, expanding said O-shaped buckle radically, so that said O-shaped buckle is elastically clamped by the enlarged inner wall portion of said axial hole of said IAJ portion, and said first cushion is an elastomer and is sandwiched between said cylindrical rod portion of said connecting part of said abutment and said based member.

Preferably, said axial hole of said IAJ portion is formed by plugging or threading an annular member into an enlarged axial hole of said IAJ portion. More preferably, said annular member comprises an elastomeric bottom plate which functions as the first cushion.

Preferably, the dental implant of the present invention further comprises a second cushion which is an elastomer, and is mounted on the cylindrical rod portion of said connecting part and is sandwiched between said IAJ portion and said receiving part of said abutment.

Preferably, said IAJ portion has a cone shape structure, said abutment is a hollow metal cap having an inner cone shape opening corresponding to the cone shape structure, and said first cushion is an hollow cone-shaped elastomer received on the cone shape structure of said IAJ portion, wherein said IAJ portion is provided with a longitudinal groove on a surface of said cone shape structure, said first cushion is provided with a slit exposing said longitudinal groove, and said abutment is provided with a protrusion correspond to said groove on a wall of said inner cone shape opening, wherein said abutment is pressed to elastically clamp the said IAJ portion with said protrusion of said abutment penetrating said slit of said first cushion and protruding into said longitudinal groove of said IAJ portion; or said longitudinal groove and said protrusion are provided at positions switched with each other.

Preferably, said substantially cylindrical hollow base member is provided with a sharpened close end opposite to said IAJ portion, and said outer surface of said wall of said base member is provided with threads. More preferably, said sharpened close end is plugged into or threaded into said substantially cylindrical hollow base member.

Preferably, said substantially cylindrical hollow base member is provided with an open drilling end opposite to said IAJ portion, and said outer surface of said wall of said base member is provided with threads.

BRIEF DESCRIPTION OF THE DRAWINGS

FIG. 1b shows a perspective view of elements/parts for assembling the dental implant shown in FIG. 1a.

FIG. 2 shows a perspective view of two parts adapted to be threadably connected to each other for forming an abutment of the dental implant shown in FIG. 1a.

FIG. 4b shows a perspective view of elements/parts for assembling the dental implant shown in FIG. 4a.

FIG. 5b shows a perspective view of elements/parts for assembling the dental implant shown in FIG. 5a.

FIG. 7b shows a perspective view of elements/parts for assembling the dental implant shown in FIG. 7a.

FIG. 8 shows an enlarged cross-sectional view of an O-shaped buckle of the dental implant shown FIG. 7a.

FIG. 9b shows a perspective view of elements/parts for assembling the dental implant shown in FIG. 9a.

DETAILED DESCRIPTION OF THE INVENTION

Typically a dental implant consists of three major components: fixture, abutment and prosthetic teeth, wherein the fixture is designed to be implanted into jawbone. Abutment serves to support the prosthetic teeth. The prosthetic teeth function as the crown of natural teeth for cutting/grinding foods and transfer bite forces to abutment and fixture.
Features and Advantages of the Present Inventive Dental Implant Design The present inventive dental implant is designed for both one-step/immediate loading and traditional two-step implantation procedures. The primary features and their respective advantages of the present inventive dental implant design are briefly described in the following:
(1) Perforated Hollow Design:

This design comprises a hollow and perforated implant case. This hollow and perforated case is preferably made from a biocompatible metallic material, such as c.p. titanium, titanium alloys, gold alloys, etc. Preferably this hollow and perforated case is made from a high strength metallic material. Preferably this case is made from a biocompatible, high strength and relatively low modulus metallic material to reduce the stress-shielding effect of the implant. Preferably this case is made from a titanium or titanium alloy. This high strength allows for much more flexible implant design, such as the proposed perforation design, different implant size and thickness limitations to withstand the occlusion force. Pure titanium, particularly grade I or grade II c.p. Ti may not be a good candidate for this hollow, perforated design due to its low strength.

Two fundamentally different methods may be utilized for the fabrication of the hollow, perforated metallic implant sheath: precision casting and precision machining. Although casting is almost always the most economical way for the fabrication of Ti/Ti alloys, challenges such as how to increase castability, decrease porosity level and casting defects, and decrease oxidation/contamination and hardened surface layer always accompany the casting processes of the highly reactive material.

Figure 1A:
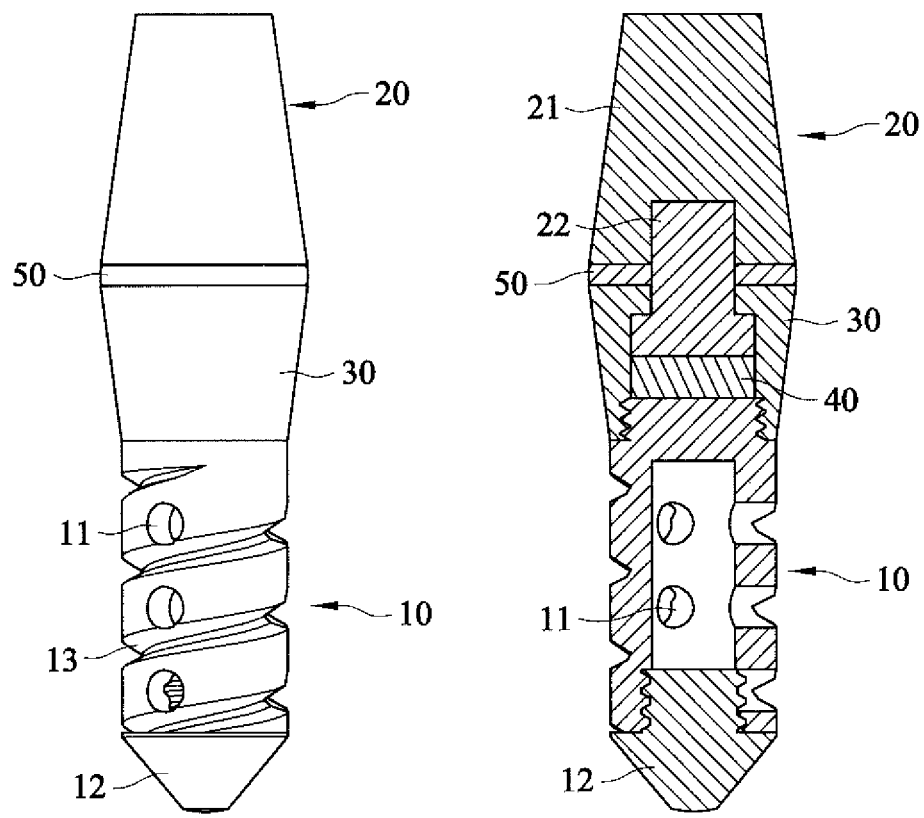
FIG. 1a shows a perspective view and a cross-sectional view of a dental implant constructed according to a first preferred embodiment of the present invention.
Figure 4A:
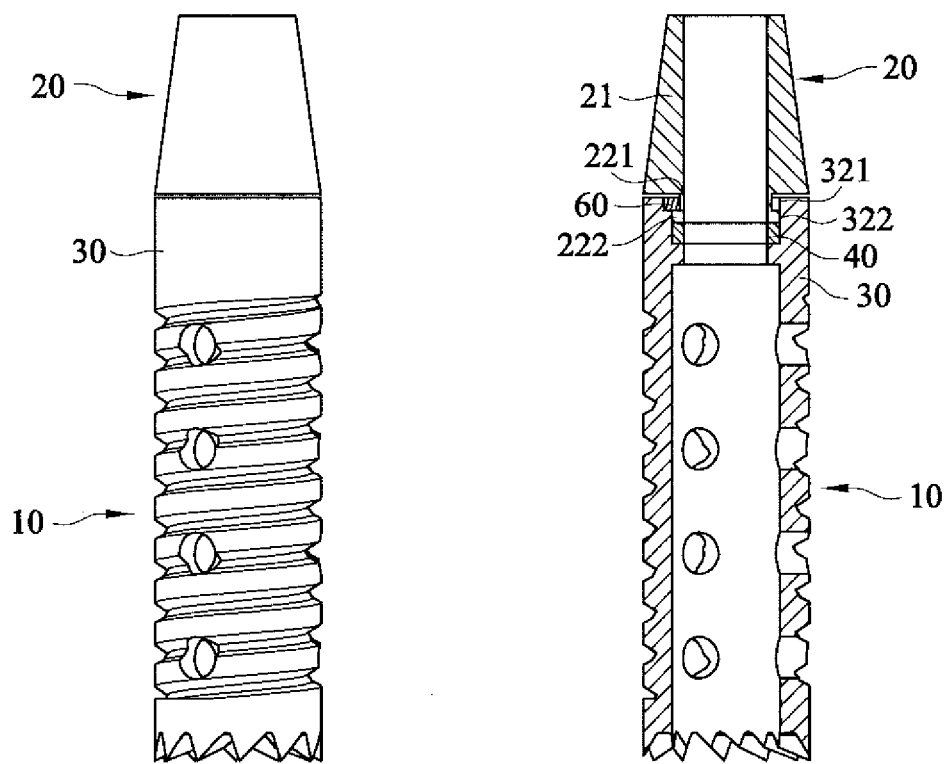
FIG. 4a shows a perspective view and a cross-sectional view of a dental implant constructed according to a third preferred embodiment of the present invention.

The perforated, hollow implant root may be a one-piece device (an example is illustratively demonstrated in FIG. 5), a two-piece device (an example is illustratively demonstrated in FIG. 1), or an open-end design (an example is illustratively demonstrated in FIG. 4). The implant-abutment junction (IAJ) may be reverse trapezoid-shaped or straight. Examples are shown in FIGS. 1*a*, and 4*a*.

Preferably this hollow and perforated implant case is filled with an osteoconductive filling material (for example, a calcium-based material). Preferably the filling material is an osteoconductive and bioresorbable material, through which new bone is conducted into the fixture core and gradually replaces the filling material, thereby establishing a firm, interlocked bond between fixture and jawbone. The filling material is preferably a Ca-based bone substitute material in the form of cement (for example, a calcium phosphate cement, a calcium sulfate cement, or a calcium phosphate/calcium sulfate composite cement), granule or block.

When a bioresorbable cement is used as filling material, the cement may be hardened before being filled into the interior (cavity) of the perforated, hollow implant (preformed), or after being injected into the implant interior. One primary advantage for the cement hardened after being inserted into the implant interior is that, during injection, the cement can flow and fill all the spaces of implant interior, including all the openings of drillings/perforations, while it is still in the form of flowable paste. The cement inside the perforations will have a direct contact with surrounding bone tissue when implanted, thus accelerating the osteoconduction process.

Optionally, the cement paste may be injected into the hollow implant right after the implant is implanted in place. In so doing, not only all the openings of drillings/perforations can be filled with the cement, the injected cement paste can also flow out of the implant interior through perforation openings into the space between implant and the surrounding bone unavoidably created during drilling of the bone. The in-filled cement between implant and the surrounding bone further enhancing the osteoconduction process.

The perforations with right sizes and distributions are designed to establish bonding between the osteoconductive filling material and the surrounding tissue at early stage. When the in-filled bioresorbable material is gradually resorbed and replaced with new bone tissues through the perforations, the implant-bone bonding will be further enhanced. This design is ideal for early or immediate loading application.

As mentioned earlier, conclusions from the literature on stress shielding and overloading effects regarding dental implant are often mixed or even conflicting. Nevertheless, no matter which effect dominates the long-term performance of dental implant, it seems logical that excessive stress concentrations (possibly resulting from non-axial overloading) plays a critical role in early-stage marginal bone loss process. The innovation of the proposed dental implant design is the concept of establishing bonding between fixture and bone not only through the exterior surface of the fixture but, more importantly, through the interior structure of the fixture so that the functional force could be transferred to the jawbone more smoothly. Due to the excellent bioactivity of the in-filled Ca-based material, new bone adaptations are expected to occur quickly onto the filling material-exposed perforation sites of implant surface at the early stage of implantation.

Furthermore, as mentioned earlier, one known factor causing failure of immediately-loaded implant is fibrous tissue encapsulation around the implant. Fibrous encapsulation growing into the space between implant and bone can endanger osseointegration of implant, leading to implant instability and eventual failure. A CPC-filled perforated-sheath implant design is be especially valuable to immediate implantation procedures which require a faster healing process.

Furthermore, this hollow, perforated design allows growth factor, stem cells, drug (for example, antibiotics), etc. to be incorporated in the filling material (preferably a porous material such as a Ca-based bone substitute, CPC, etc.). Few existing dental implant designs can do the job.

A further advantage of the hollow, perforated design is that, as needed, during drilling cooling water can be flowed in and out the hollow implant through the openings to avoid overheating the device. Again, few existing dental implant designs can do the job.

(2) Cushion/Buffer Design

One critical factor leading to dental implant loosening is the non-uniform occlusive force on the root. As mentioned earlier, in natural teeth the periodontal ligament functions as a cushion/buffer between tooth and jawbone, absorbing impact force and uniformly transferring occlusal forces to surrounding bone. Due to lack of periodontal ligament, dental implant has to directly bond to bone, causing non-uniform stress distribution in bone which might lead to implant failure.

Designs incorporating mechanisms able to reduce the negative effects of the non-uniform stress distribution in the alveolar bone include that distributes stresses more uniformly (avoiding stress-concentrated spots) and that absorbing stresses more effectively (simulating the cushion function of periodontal ligament.)

The cushion design of this invention comprises a shock-absorbing elastomer cushion between IAJ and abutment. The cushion design simulates the function of periodontal ligament, which reduces the impact effect on the surrounding alveolar bone. The applied occlusion force on abutment can be at least partially transmitted to the cushion.

This shock-absorbing elastomer is preferably made from a polymer-based material, more preferably from a rubber-based material, such as PTFE, PU, PP, etc. This elastomer can effectively absorb the impact (biting) force, thus reducing the negative effect of occlusive force on bone/teeth.

Figure 6:
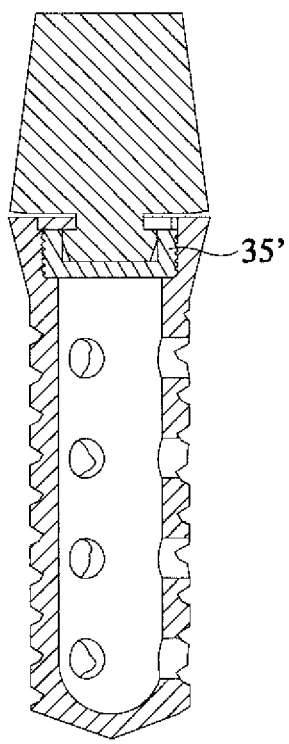
FIG. 6 shows a cross-sectional view of a dental implant constructed according to a fifth preferred embodiment of the present invention.

The elastomer cushion may be a single layer, substantially flat, solid, hollow or porous plate, preferably in round shape. The elastomer cushion may also be a multilayer design. The elastomer cushion may also be a one-piece U-shaped (or bowl-shaped three-dimensionally) design. An example is shown in FIG. 6.

The elastomer cushion may also be a hollow cylinder or cone-shaped design. Examples are shown in FIGS. 4 and 9.

The cone-shaped cushion is first set on top of the implant, and then place the metal housing above the cushion on the outside. The metal housing has protruding positioning points that fit into grooves on a surface of the IAJ. Align and fit the metal housing until it clicks. This latch fixes the metal housing in position so it does not rotate (FIG. 9). In this example, the cone-shaped cushion is sandwiched between the IAJ and the metal housing.

Alternatively, the metal housing may be bonded to the crown as a one-piece element in advance, wherein the cone-shaped cushion (buffer) is placed on the IAJ surface and its outer surface is directly bonded to the one-piece element of the metal housing and the crown.

In doing so, the abutment (metal housing) movement is confined within the groove. When any occlusion force is applied onto the metal housing, at least part of the force is absorbed by the cone-shaped cushion.

One primary advantage of these cushion designs is that all the cushions are easily removable, maintainable, and replaceable without damaging or disrupting the implant root or surrounding bone. This replaceable feature is crucial, since the cushion—no matter being made from polymer or metal—is subject to mechanical and/or thermal fatigue, plastic deformation when it is used for an extended period of time.

When a curable or hardenable cushion (for example, a polymer or rubber type cushion prepared from mixing and curing a matrix agent and a hardening agent) is used, the cushion material may be cured (pre-formed) and shaped before being inserted between the IAJ and the abutment (pre-formed). The cushion material may also be cured after being inserted between the IAJ and the abutment, i.e., putting the cushion material in place—between IAJ and abutment—while the cushion material is not fully cured and is still flowable and moldable. One advantage of this in-situ curing method is that the fitness of the cushion between IAJ and abutment is improved and the stress distribution is more effective and uniform.

(3) Bendable C-Shaped Buckle and Protruding Inner Wall O-Shaped Buckle

To lock abutment in place, a bendable/removable C-shaped buckle with a smooth inner wall and an O-shaped buckle with a protruding inner wall are designed. Due to the smooth inner wall (surface), the C-shaped buckle design allows free vertical movement of abutment/tooth. Anchors (preferably multiple anchors) on the outer surface of the C-shaped buckle are so designed that the abutment is securely and stably locked in place. Examples of a C-shaped buckle are shown in FIGS. 4-6. The C-shaped buckle is preferably made from a highly elastic material, more preferably from a highly elastic metallic material, so that when the buckle is bent to facilitate installation or removal of the buckle, little plastic (permanent) deformation occurs.

FIG. 4 is an example of an open-end, tubular type dental implant assembly comprising a C-shaped buckle for two-step self-tapping implantation procedure.

FIG. 5 is an example of a close-end type dental implant assembly comprising a C-shaped buckle for two-step implantation procedure. During first procedure, the implant root is implanted in alveolar bone, the cushion/buffer is inserted into the implant root, and the C-type buckle is mounted onto the abutment. During second procedure, the abutment is installed with the C-type buckle in an enlarged hole of the IAJ, which is then locked by the C-type buckle when the C-type buckle is pushed into the enlarged hole of the IAJ and is radically deformed inwardly.

Figure 7A:
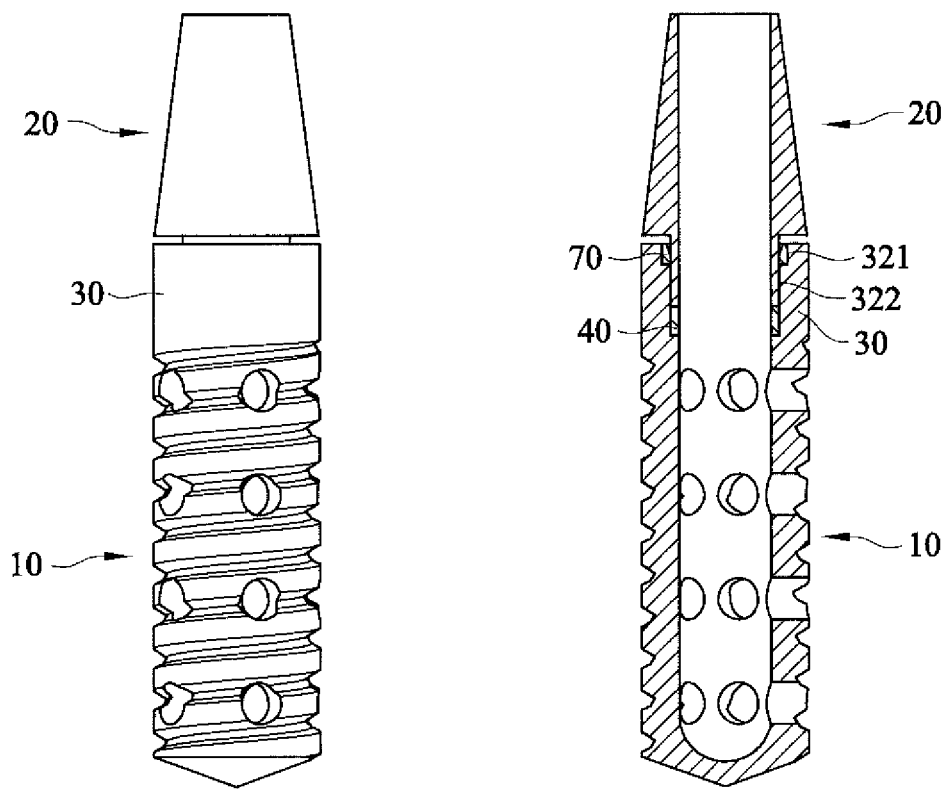
FIG. 7a shows a perspective view and a cross-sectional view of a dental implant constructed according to a sixth preferred embodiment of the present invention.
Figure 7B:
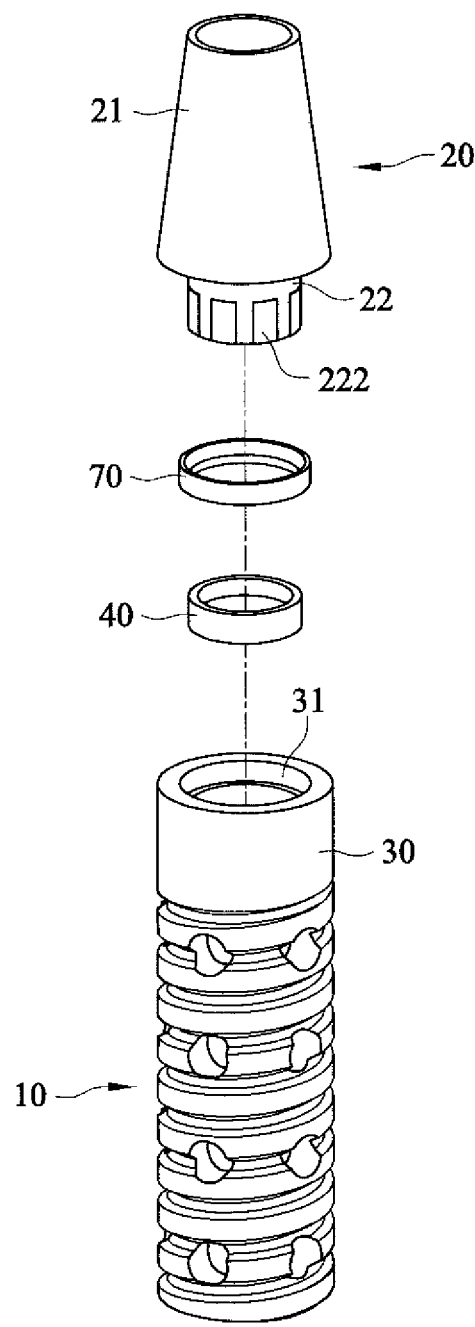
Figure 8:
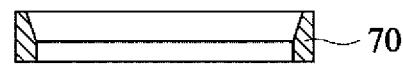

An example of a dental implant assembly comprising an O-shaped buckle with a protruding inner wall is shown in FIGS. 7 and 8. After the cushion is put in place, the O-shaped buckle is installed. The abutment can then be slid ("clicked") into the hole of the implant root through the slightly protruding wall of the buckle.

EXAMPLES

Figure 1B:
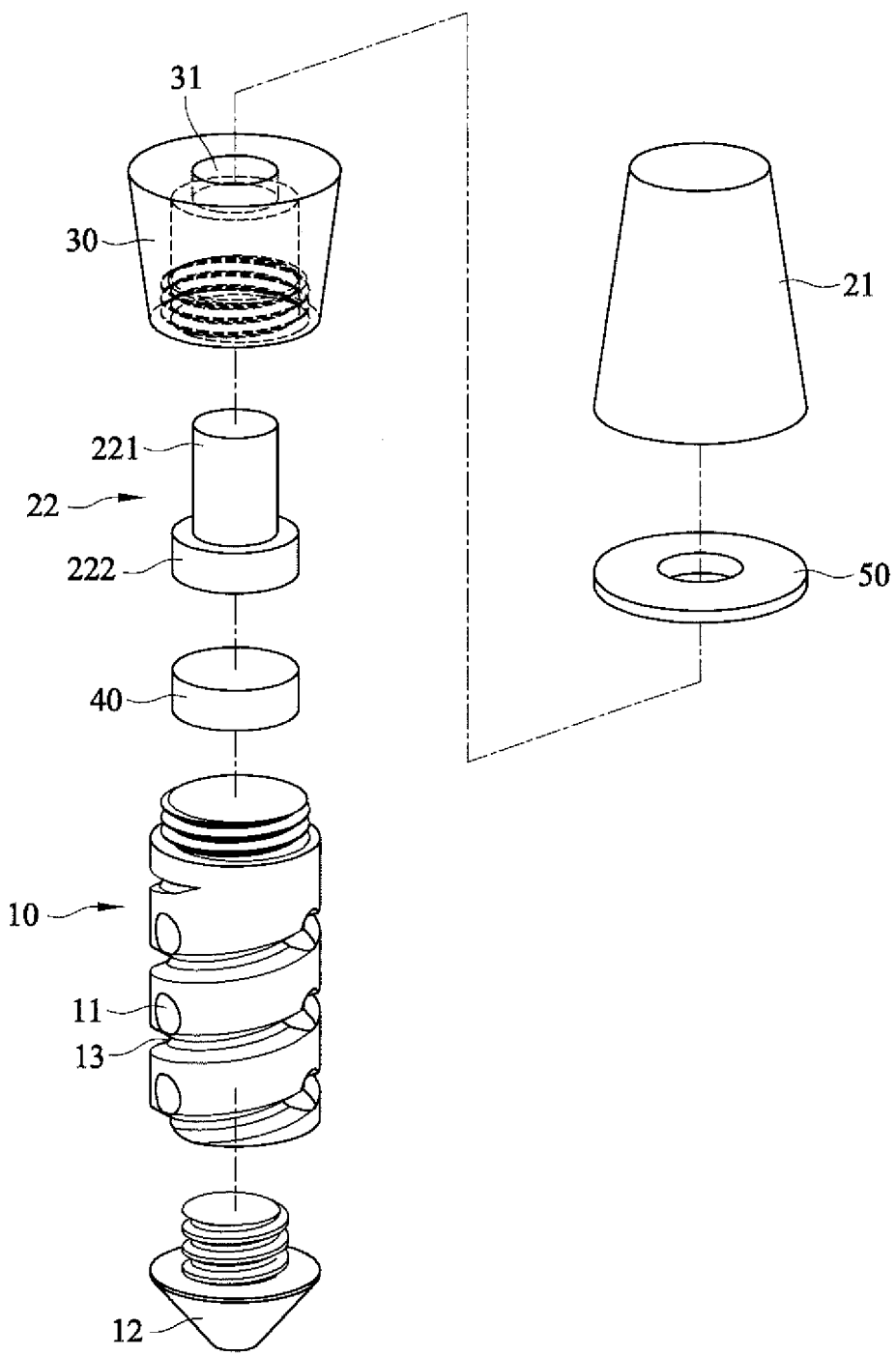

A dental implant constructed according to a first preferred embodiment of the present invention is shown in FIGS. 1a and 1b, which has a substantially cylindrical hollow base member 10 comprising a wall defining a space in said substantially cylindrical hollow base member, and a plurality of through-thickness-holes 11 communicating said space with an outer surface of said wall; an abutment 20; an implant-abutment junction (IAJ) portion 30 at a top end of said base member to retain said abutment 20 to said base member 10, so that said abutment 20 is able to move within a predetermined distance alone an axial direction of said base member 10.

Said abutment 20 has a receiving part 21 for receiving a dental prosthesis and a connecting part 22, wherein said IAJ portion 30 has an axial hole 31 and said connecting part 22 of said abutment has a cylindrical rod portion 221 having a diameter corresponding said axial hole 31 and an enlarged end 222 extending from said cylindrical rod portion, wherein said cylindrical rod portion 221 is slidably received in said axial hole 31 of said IAJ portion 30 with said enlarged end 222 protruding from the bottom end of said axial hole 31 and the top end of said cylindrical rod portion protruding from the top end of said axial hole 31. Said IAJ portion 30 is a separate part and threadedly connected to said top end of said base member 10, preventing said abutment 20 from escaping said IAJ portion 30. A first cushion 40 which is a round plate made of elastomer and is put on the top end of the base member 10 before said IAJ portion 30 is threadedly connected to said top end of said base member 10. The first cushion 40 is sandwiched between said enlarged end 222 of said connecting part 22 of said abutment 20 and the top end of said base member 10 for providing a resistance force when said abutment 20 is pressed to move relatively toward said base member 10 and providing a bouncing back force when said abutment 20 is released from said pressing Said substantially cylindrical hollow base member 10 is provided with a sharpened close end 12 opposite to said IAJ portion 30, and said outer surface of said wall of said base member is provided with threads 13. Said sharpened close end 12 is threaded into a bottom end of said substantially cylindrical hollow base member 10.

Figure 2:
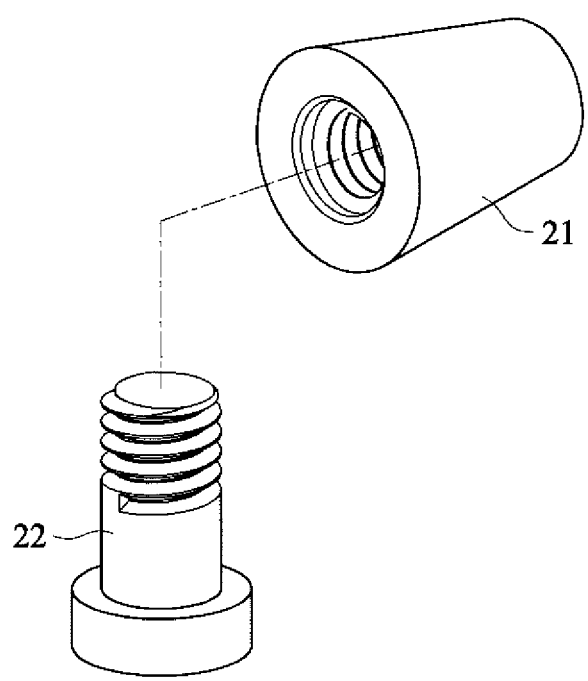

The dental implant further comprises a second cushion 50 which is a ring made of an elastomer, and is mounted on the cylindrical rod portion 221 of said connecting part 22 and is sandwiched between said IAJ portion 30 and said receiving part 21 of said abutment 20. The cylindrical rod portion 221 of said connecting part 22 is plugged into a corresponding recess at a bottom of said receiving part 21 of said abutment 20. Alternatively, said connecting part 22 of said abutment 20 is threadedly connected to said receiving part 21 of said abutment 20 as shown in FIG. 2.

Figure 3:
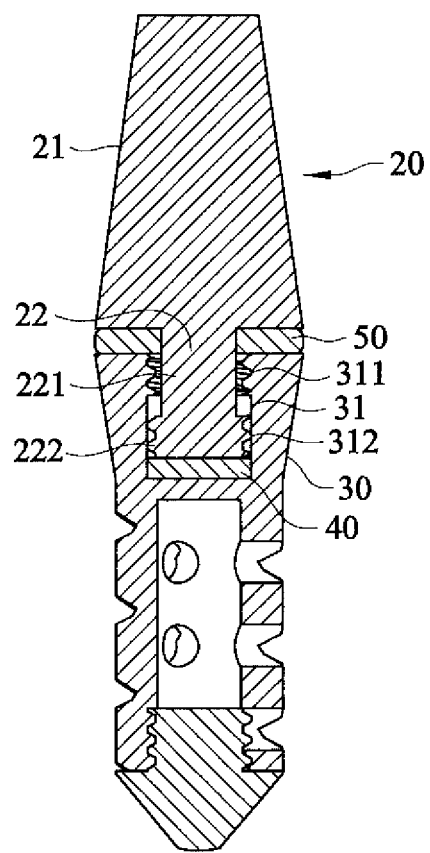
FIG. 3 shows a cross-sectional view of a dental implant constructed according to a second preferred embodiment of the present invention.

A dental implant constructed according to a second preferred embodiment of the present invention is shown in FIG. 3, which is similar to the first preferred embodiment shown in FIGS. 1a and 1b except that the abutment 20 and the IAJ portion 30. As shown in FIG. 3, said abutment 20 has a receiving part 21 and a connecting part 22 integrally extending from a bottom of said receiving part 21. The connecting part 22 has a cylindrical rod portion 221 and an enlarged threaded end 222 extending from said cylindrical rod portion 221, wherein said IAJ portion 30 has an axial hole 31 having a threaded inner wall portion 311 corresponding to said an enlarged threaded end 222 and a smooth inner wall portion 312 following the threaded inner wall portion 311 having a diameter slightly larger than that of said enlarged threaded end 222, wherein said enlarged threaded end 222 is threaded through the threaded inner wall portion 311 and into the smooth inner wall portion 312 of said axial hole 31. The first cushion 40 and the second cushion 50 are mounted similarly to those shown in FIGS. 1a and 1b.

Figure 4B:
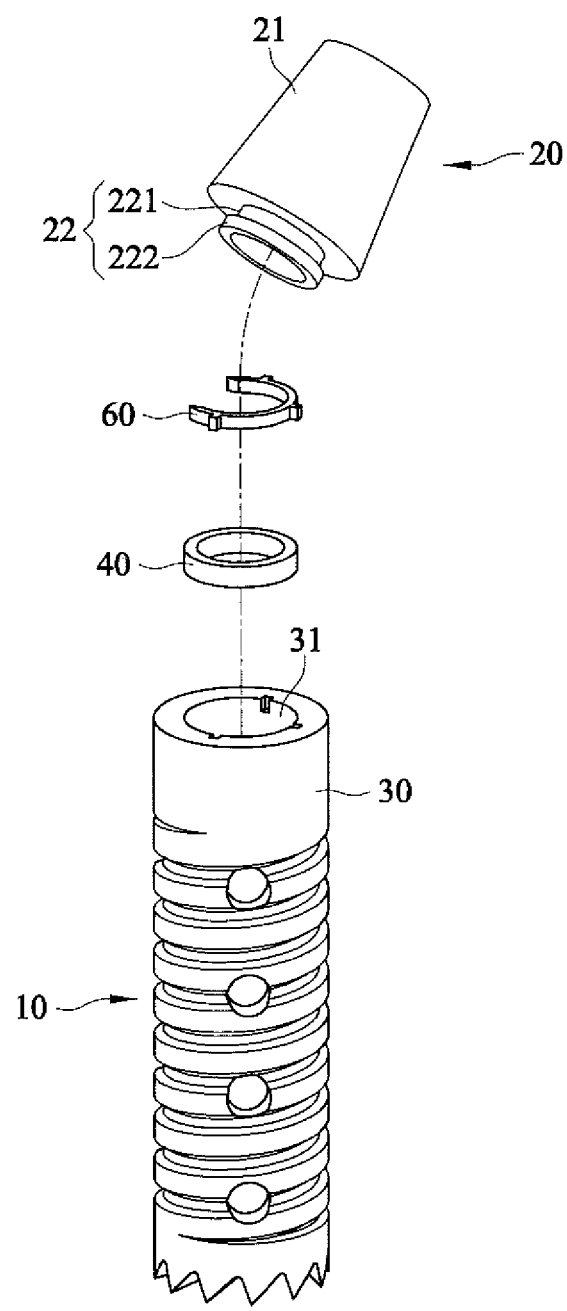

A dental implant constructed according to a third preferred embodiment of the present invention is shown in FIGS. 4a and 4b, wherein a C-shaped buckle 60 is used to retain an abutment 20 to a substantially cylindrical hollow base member 10. Said abutment 20 has a receiving part 21 and a connecting part 22 having a cylindrical rod portion 221 and an enlarged end 222 extending from said cylindrical rod portion, wherein said C-shaped buckle 60 is mounted on the cylindrical rod portion 221 and between the enlarged end 222 and the receiving part 21 of said abutment 20. IAJ portion 30 has an axial hole 31 having an enlarged inner wall portion 321 corresponding to said C-shaped buckle 60 and a smooth inner wall portion 322 following the enlarged inner wall portion having a diameter corresponding to that of said enlarged end 222. A first cushion 40 which is a ring made of an elastomer is placed in the smooth inner wall portion 322 of the axial hole 31, and then said connecting part 22 of said abutment 20 is forced to insert into the axial hole 31 of the IAJ portion 30, so that said C-shaped buckle 60 is elastically clamped by the enlarged inner wall portion 321 of said axial hole 31 of said IAJ portion 30, whereby the first cushion 40 is sandwiched between said enlarged end 222 of said connecting part 22 of said abutment 20 and said based member 10. In the embodiment, said substantially cylindrical hollow base member 10 is provided with an open drilling end opposite to said IAJ portion 30.

Figure 5A:
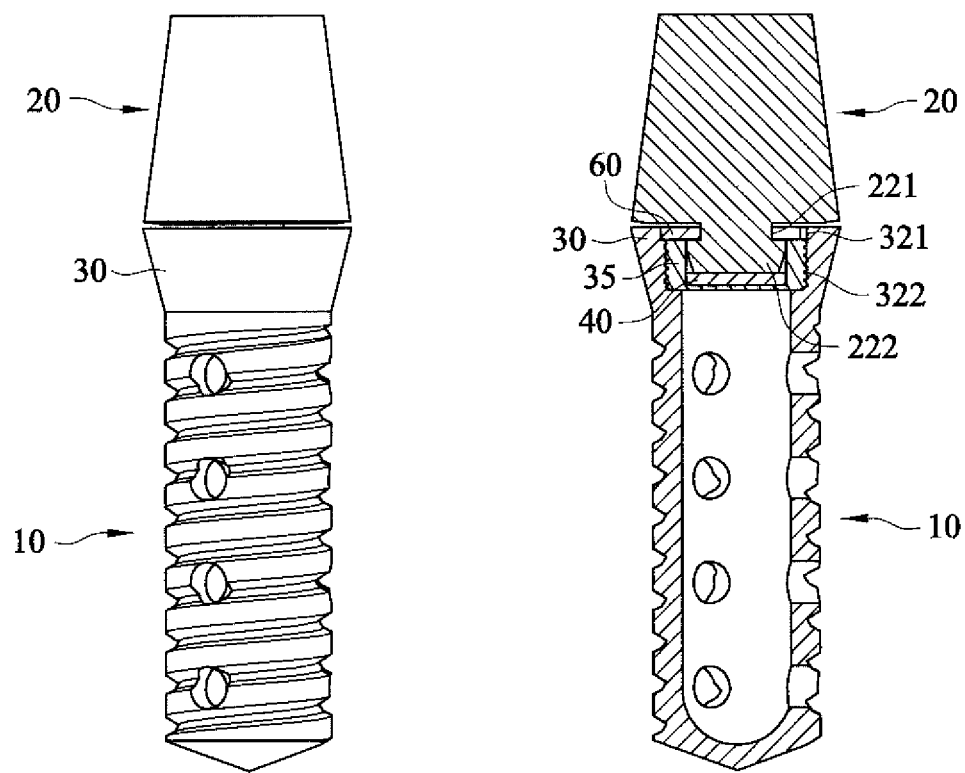
FIG. 5a shows a perspective view and a cross-sectional view of a dental implant constructed according to a fourth preferred embodiment of the present invention.
Figure 5B:
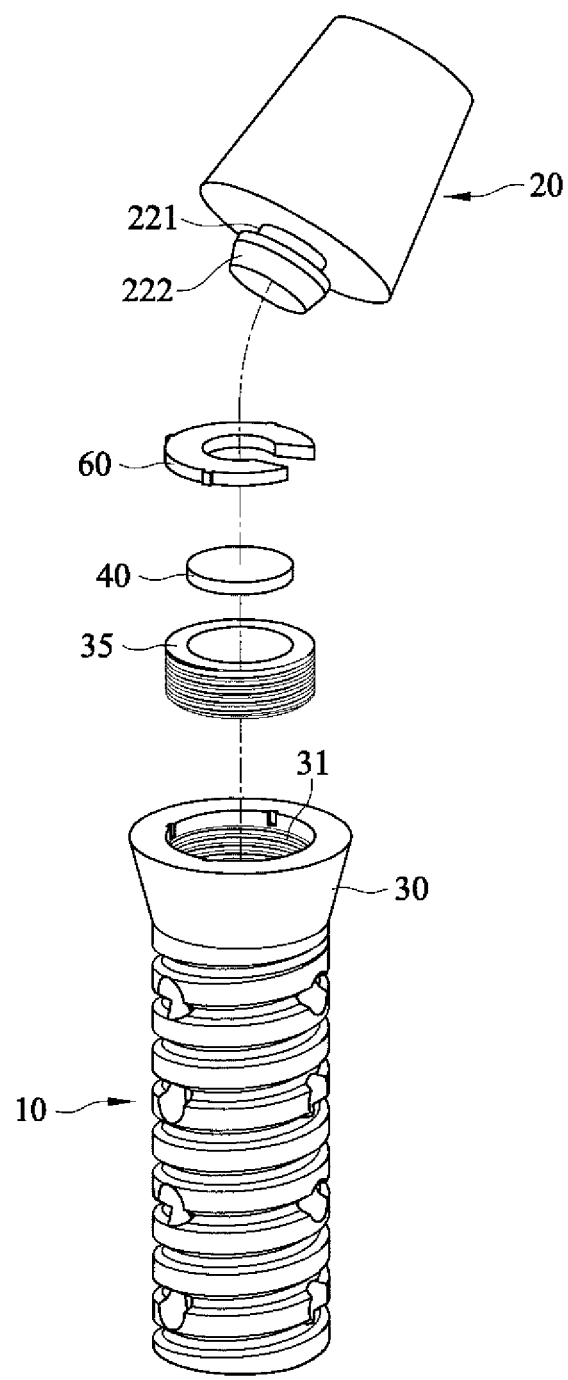

A dental implant constructed according to a fourth preferred embodiment of the present invention similar to the third preferred embodiment shown in FIGS. 4a and 4b is shown in FIGS. 5a and 5b, wherein like elements or parts are represented by like numerals. In this fourth embodiment, a relatively large axial hole 31 of the IAJ portion 30 is threadedly engaged with a metallic annular member 35, so that an enlarged inner wall portion 321 corresponding to a C-shaped buckle 60 and a smooth inner wall portion 322 following the enlarged inner wall portion having a diameter corresponding to that of an enlarged end 222 of an abutment 20 are formed. A first cushion 40 which is a round plate made of an elastomer is placed inside the annular member 35, and then the C-shaped buckle 60 and the abutment 20 are connected to the IAJ portion 30 of the base member 10 similarly to those shown in FIGS. 4a and 4b.

In a dental implant constructed according to a fifth preferred embodiment of the present invention shown in FIG. 6, said metallic annular member 35 shown in FIGS. 5a and 5b is replaced by a similar annular member 35 made of an elastomer. In this case, the first cushion 40 used in FIGS. 5a and 5b is omitted.

A dental implant constructed according to a sixth preferred embodiment of the present invention shown in FIGS. 7a and 7b, wherein an O-shaped buckle 70 is used to retain an abutment 20 to a substantially cylindrical hollow base member 10. Said abutment 20 has a receiving part 21 for receiving a dental prosthesis and a connecting part 22 having a cylindrical rod portion 222. IAJ portion 30 has an axial hole 31 having an enlarged inner wall portion 321 near an entrance of said axial hole and a smooth inner wall portion 322 following the enlarged inner wall portion having a diameter corresponding to that of said cylindrical rod portion 222. Said O-shaped buckle 70 has an inner diameter slightly smaller than that of the cylindrical rod portion 222 and an outer diameter slightly smaller than that of the enlarged inner wall portion 321 of said axial hole 31. A first cushion 40 which is a ring made of an elastomer is placed in the smooth inner wall portion 322 of the axial hole 31, and then said cylindrical rod portion 222 of said connecting part 22 of said abutment 20 is forced to insert into said O-shaped buckle 70 placed in the enlarged inner wall portion 321 of said axial hole 31, expanding said O-shaped buckle radically, so that said O-shaped buckle 70 is elastically clamped by the enlarged inner wall portion 321 of said axial hole 31 of said IAJ portion 30. The first cushion 40 is sandwiched between said cylindrical rod portion 222 of said connecting part 22 of said abutment 20 and said based member 10.

As shown in FIG. 8, the inner wall of said O-shaped buckle 70 has a slant surface to facilitate the insertion of the cylindrical rod portion 222 of said connecting part 22 of said abutment 20.

Figure 9A:
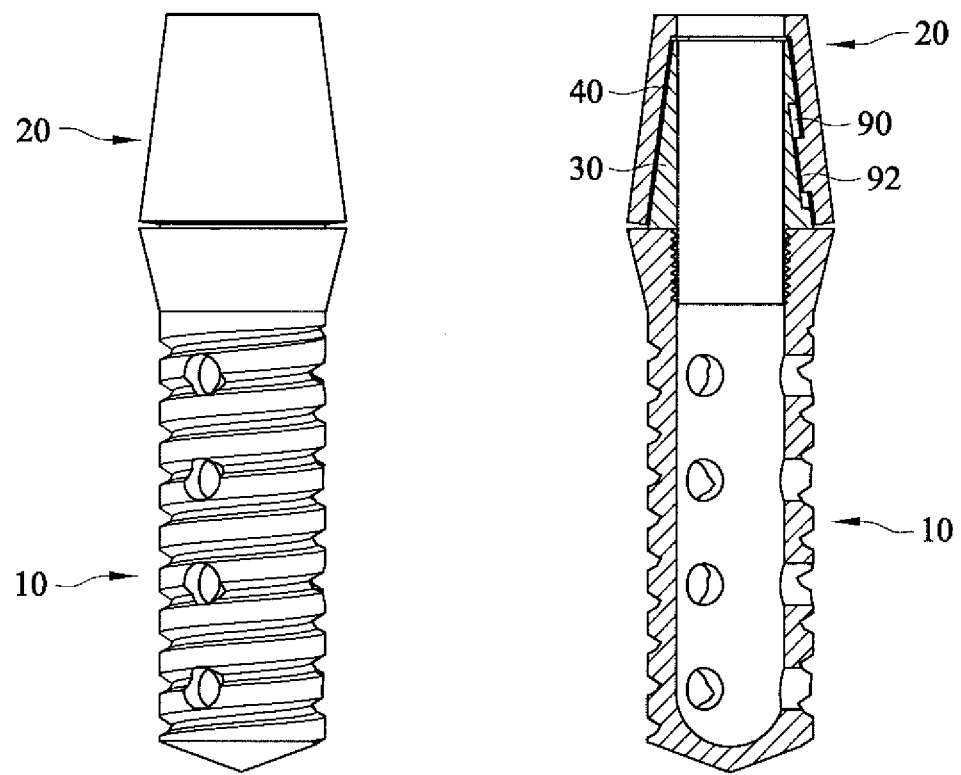
FIG. 9a shows a perspective view and a cross-sectional view of a dental implant constructed according to a seventh preferred embodiment of the present invention.
Figure 9B:
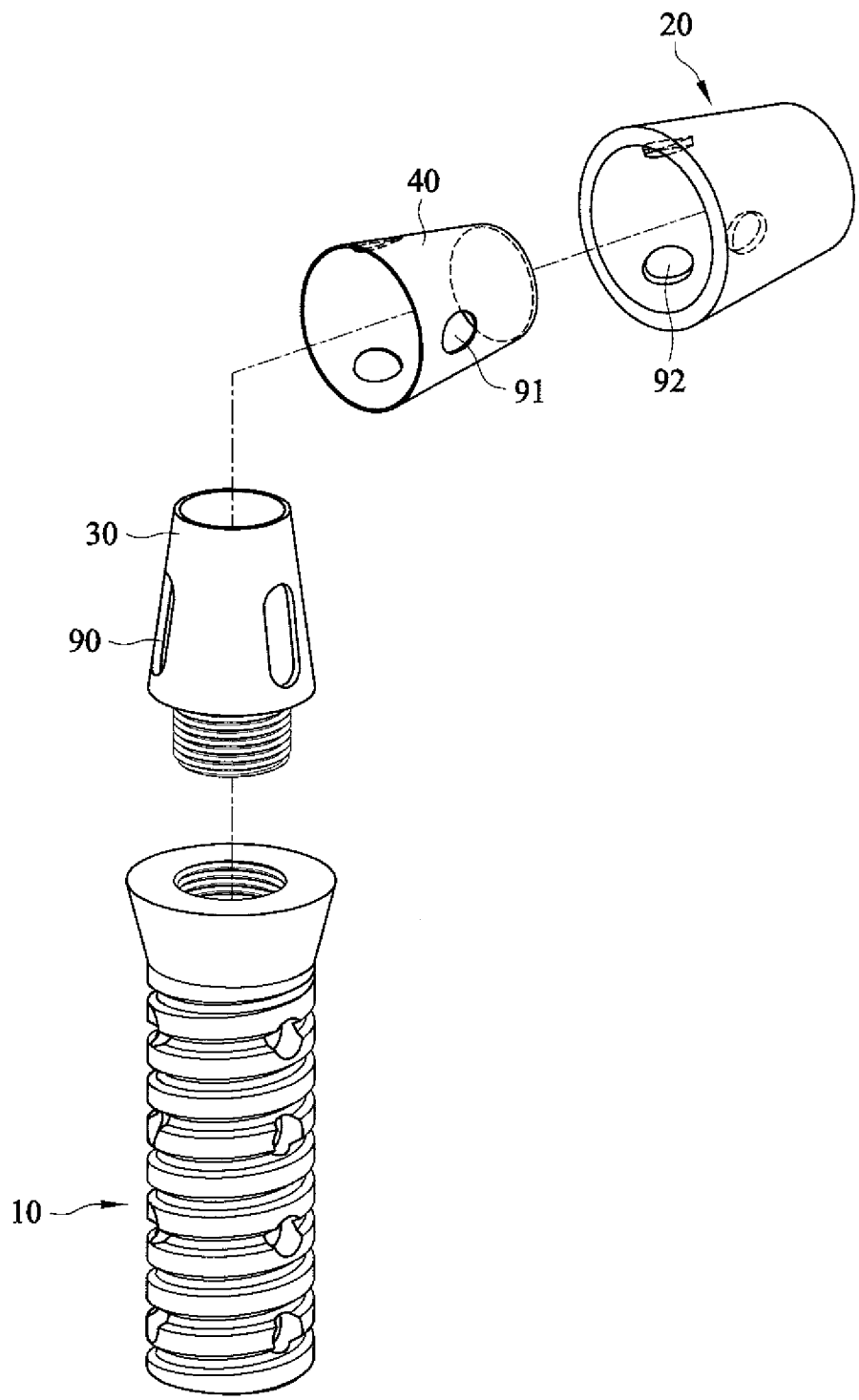

A dental implant constructed according to a seventh preferred embodiment of the present invention shown in FIGS. 9a and 9b, which includes a substantially cylindrical hollow base member 10, an IAJ portion 30 having a cone shape structure threadedly connected to the base member 20, an abutment 20 which is a hollow metal cap having an inner cone shape opening corresponding to the cone shape structure, and a first cushion 40 which is an hollow cone-shaped elastomer received on the cone shape structure of said IAJ portion 30. Said IAJ portion 30 is provided with three longitudinal grooves 90 on a surface of said cone shape structure, said first cushion 40 is provided with three holes 91 exposing said longitudinal grooves 90, and said abutment 20 is provided with three protrusions 92 correspond to said grooves 90 on a wall of said inner cone shape opening, wherein said abutment 20 is pressed to elastically clamp the said IAJ portion 30 with said protrusions 92 of said abutment penetrating said holes 91 of said first cushion 40 and protruding into said longitudinal grooves 90 of said IAJ portion 30. The first cushion 40 is sandwiched between the abutment 20 and the IAJ portion 30.

Figure 10:
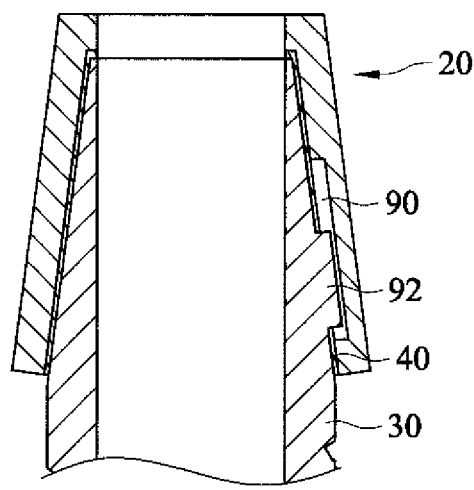
FIG. 10 shows a cross-sectional view of a dental implant similar to the dental implant shown in FIG. 9a except the longitudinal groove and the protrusion are provided at positions switched with each other.

Alternatively, said longitudinal grooves 90 and said protrusions 92 in FIGS. 9a and 9b can be provided at positions switched with each other as shown in FIG. 10. In FIG. 10, said longitudinal grooves 90 are formed on the wall of the inner cone shape opening of the abutment 20, and said protrusions 92 are formed on the surface of said cone shape structure of said IAJ portion 30. The first cushion 40 is sandwiched between the abutment 20 and the IAJ portion 30 similarly as in FIGS. 9a and 9b.

Figure 11:
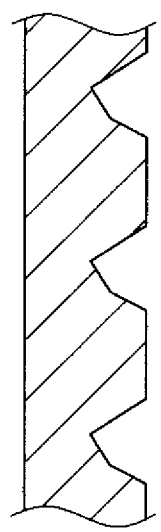
FIG. 11 shows a partial cross-sectional view of a thread design on an outer surface of a base member of a dental implant according to the present invention.

In order to improve implant-bone bonding, one or more surfaces/facets are introduced to the thread design of the substantially cylindrical hollow base member of the present invention. FIG. 11 shows an example for the thread design on an outer surface of the substantially cylindrical hollow base member according to the present invention. The implant-bone contact area according to the thread design in FIG. 11 is increased by at least about 30% in comparison with the regular thread designs.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

The invention claimed is:
1. A dental implant comprising:
a substantially cylindrical hollow base member comprising a wall defining a space in said substantially cylindrical hollow base member, and a plurality of through-thickness holes communicating said space with an outer surface of said wall;
an abutment;
an implant-abutment junction (IAJ) portion at one end of said base member to retain said abutment to said base member, so that said abutment is able to move within a predetermined distance along an axial direction of said base member;

a first flat cushion adapted to be sandwiched between said abutment and said base member in the axial direction of said base member for providing a resistance force when said abutment is pressed to move relatively toward said base member and providing a bouncing back force when said abutment is released from said pressing, wherein said abutment comprises a receiving part for receiving a dental prosthesis and a connecting part, wherein said IAJ portion has an axial hole and said connecting part of said abutment has a cylindrical rod portion having a diameter corresponding to said axial hole and an enlarged end extending from said cylindrical rod portion, wherein said cylindrical rod portion is slidably received in said axial hole of said IAJ portion with said enlarged end protruding from one end of said axial hole and another end of said cylindrical rod portion protruding from the other end of said axial hole, wherein said IAJ portion is a separate part and threadedly connected directly to said one end of said base member, preventing said abutment from escaping said IAJ portion, and said first flat cushion is a flat elastomer and is sandwiched between said enlarged end of said connecting part of said abutment and said base member; and a second flat cushion which is a flat elastomer, and is mounted on the cylindrical rod portion of said connecting part and is sandwiched between said IAJ portion and said receiving part of said abutment.

2. The dental implant of claim 1, wherein said substantially cylindrical hollow base member is provided with a sharpened close end opposite to said IAJ portion, and said outer surface of said wall of said base member is provided with threads.

3. The dental implant of claim 2, wherein said sharpened close end is plugged into or threaded into said substantially cylindrical hollow base member.

4. The dental implant of claim 1, wherein said substantially cylindrical hollow base member is provided with an open drilling end opposite to said IAJ portion, and said outer surface of said wall of said base member is provided with threads.

* * * * *